(12) United States Patent
Mönkmeyer

(10) Patent No.: US 7,267,549 B2
(45) Date of Patent: Sep. 11, 2007

(54) SET OF TEETH

(75) Inventor: Ulrich Mönkmeyer, Cala D'Or (ES)

(73) Assignee: Dental Consulting Monkmeyer S.L., Cala d'Or (ES)

( * ) Notice: Subject to any disclaimer, the term of this patent is extended or adjusted under 35 U.S.C. 154(b) by 100 days.

(21) Appl. No.: 10/499,577

(22) PCT Filed: Dec. 17, 2002

(86) PCT No.: PCT/EP02/14429

§ 371 (c)(1),
(2), (4) Date: Dec. 30, 2004

(87) PCT Pub. No.: WO03/055409

PCT Pub. Date: Jul. 10, 2003

(65) Prior Publication Data

US 2005/0095559 A1 May 5, 2005

(30) Foreign Application Priority Data

Dec. 23, 2001 (DE) ................. 101 63 105

(51) Int. Cl.
*A61C 13/08* (2006.01)
(52) U.S. Cl. ..................................... 433/197
(58) Field of Classification Search ........... 433/197, 433/198, 202.1
See application file for complete search history.

(56) References Cited

U.S. PATENT DOCUMENTS

| | | | | |
|---|---|---|---|---|
| 2,620,562 A | * | 12/1952 | Folsom | 433/197 |
| 3,252,220 A | * | 5/1966 | Goddard | 433/197 |
| 4,642,052 A | * | 2/1987 | Carlson | 433/189 |
| 5,733,125 A | * | 3/1998 | Foser | 433/197 |
| 5,951,289 A | * | 9/1999 | Kura et al. | 433/202.1 |
| 6,533,581 B1 | * | 3/2003 | Moenckmeyer | 433/197 |

* cited by examiner

*Primary Examiner*—Cary E. O'Connor
(74) *Attorney, Agent, or Firm*—The Small Patent Law Group; Dean D. Small

(57) ABSTRACT

A set of pre-manufactured teeth are provided and include, at least one of a first molar or premolar selected from a group of molars or premolars provided for one jaw, and at least one of a second premolar or molar selected from a group of antagonists provided for the other jaw, wherein at least three centric contact points being provided in each case of a fossa of a premolar or a molar, a stamp cusp of the antagonist coming to rest on the contact points in the position of intercuspation, the contact points being disposed on a compensation curve defined by the movement of the jaw condyles, the centric contact points each lying on a spherical sector, and abrasions being disposed in at least one movement track without breaking up the punctiform contacts.

13 Claims, 4 Drawing Sheets

SET OF TEETH

CROSS REFERENCE TO RELATED APPLICATIONS

This application is a filing under 35 U.S.C. 371 of PCT/E02/14429 filed Dec. 17, 2002, which claims the benefit of German Application DE 101 63 105.7, filed Dec. 23, 2001.

BACKGROUND OF THE INVENTION

The invention relates to a set of pre-manufactured teeth.

In dentistry, occlusion is the usual term for the contact between teeth of the upper jaw and teeth of the lower jaw. In reconstruction of an occlusion and thus of a masticatory surface, the aim is to ensure that the tooth contacts occur uniformly and simultaneously in all four support zones and that, upon functional movements (primarily protrusion, laterotrusion and mediotrusion movements) of the lower jaw relative to the upper jaw, uninterrupted sliding is obtained between all antagonist posterior teeth. This applies nowadays to individual rehabilitation.

The various occlusion concepts are named for their characteristics in respect of centric contact (point-centric, long-centric, freedom-in-centric) and in respect of the relationships in laterotrusion, mediotrusion and protrusion (cuspid guidance, group guidance). The added consideration of the relationships on the mediotrusion side (balance side) led to the various occlusion concepts being divided into three main groups:
1. fully balanced occlusion types
2. unilaterally balanced occlusion types, and
3. occlusion types with anterior/cuspid guidance.

The early occlusion concepts arose in the context of the problem of complete denture prosthetics. From the aim of positioning the prosthesis as steadily as possible against tilting in order to secure the adhesive anchoring, fully balanced concepts were necessarily developed in which the importance of individual functional elements was ignored.

Consequently, the factory-made teeth developed for these methods had no functional masticatory surfaces. The concept of organic occlusion qualified the importance of the contacts present in the excursive movements. It starts from the premise that excursions are not guided by the teeth in the masticating movement.

A uniform occlusion concept for complete denture prosthetics and the natural bite has not as yet been postulated. The hope of finding the ideal occlusion concept by describing the natural state, through data from anthropological studies, has also come to nothing.

The principles of the "freedom-in-centric" concept are that the cusps are fixed as far as possible through three-point contacts on a flat area in the central fossa which is not provided by nature but instead has been formed either on the basis of an individually modeled restoration or by grinding.

The concept of "organic disclusion" is based on a mutually protective function of anterior and posterior teeth. For individual restoration, this is nowadays the most widely used technique since, through the additive technique, it yields much more precise wax modeling results than does subtractive shaping.

It is only recently that the resulting modern requirements for individual functional masticatory surfaces have been postulated. The properties of factory-made teeth for the removable denture have also been recently described. In particular, the combination of the study of the natural model with geometric and mechanical considerations has led to the concept of the inductive-deductive functional masticatory surface.

Since the principle of additive shaping cannot be applied in the production of an individual denture with factory-made teeth, these have to be pre-manufactured in such a way that they can be tailored individually in the subtractive method. The postulated arrangement, in this connection, of the antagonist contacts in relation to the sagittal and transverse compensation curve has led to the development of teeth which are supported vertically in the position of intercuspation and which function in the fully balanced occlusion concept, the unilaterally balanced occlusion concept, and the anterior/cuspid guided occlusion concept. Such sets of teeth are known, for example, from PCT/EP99106079 (hereafter Mönkmeyer) which describes sets of teeth in which the stamp cusps of an antagonist in the intercuspation position come to rest on three or more contact points in the fossa of the other antagonist. The contact points are disposed on a sagittal and transverse compensation curve defined by the movement of the jaw condyles. Such sets of teeth can also be set up in tooth-to-tooth relationship, for example one tooth to two teeth, in class I, II and III cases and in cross-bite (Mönkmeyer).

In order to avoid laterotrusion and mediotrusion disturbances in any event, and to ensure a harmonious take-over of the guide surfaces in the event of abrasion phenomena, it is recommended for the individual restoration to include a disclusion of the posterior teeth which increases uniformly from anterior to posterior. This is achieved by having the inclination of the cusp slopes decrease sequentially by 5° per tooth.

Abrasion teeth are also known wherein the abrasions simulate a natural abrasion state by contact surfaces being formed from original contact points.

The discussion of the occlusion concepts is closely associated with the phenomenon of abrasion and attrition. The question of to what extent abrasion and attrition can be classified as a physiological or pathological phenomenon has not as yet been fully clarified.

Factory-made teeth derived from these requirements of individual prosthetics should anticipate abrasion processes. Abrasion processes in the context of occlusion are highly sensitive processes. So-called abrasion teeth do not satisfy this demand because their abrasions are not methodically connected to the processes in the complex stomatognathic system. It has been argued that the central problem in this context is the loss of the central relationship.

BRIEF DESCRIPTION OF THE INVENTION

Various embodiments of the invention make available sets of teeth which, upon functional movements of the lower jaw with respect to the upper jaw, permit uninterrupted sliding between all antagonist posterior teeth, without losing the central relationship in the vertical and horizontal, and which can be factory-made and can be tailored individually in the subtraction technique.

According to various embodiments of the invention, a set of pre-manufactured teeth are provided that include at least one first molar or premolar selected from a group of molars or premolars provided for one jaw, and at least of one second premolar or molar selected from a group of antagonists provided for the other jaw, at least three centric contact points being provided in each case in the fossa of a premolar or molar, a stamp cusp of the antagonist coming to rest on the contact points in a position of intercuspation, and the contact points being disposed on a compensation curve defined by the movement of the jaw condyles. The set of teeth provide centric contact points that each lie on a spherical sector, and abrasions are disposed in at least one movement track without breaking up at least one of the punctiform contacts. The abrasions can also be so arranged that more than one or all punctiform contacts are maintained.

Based on inductive and deductive considerations, natural unabraded dentitions were therefore copied, brought into occlusion in jaw simulators according to the rules of the art, and checked for their suitability in respect of the discussed occlusion concepts. The results show that these natural teeth function only very limitedly according to the different systems. The teeth were then modifed in the sense of PCT/EP06079. The stamp cusps and the fossa were altered in such a way that each stamp cusp comes to rest on three points of its antagonist fossa in centric relationship (IKP). These bearing points were designed as spherical-sector-shaped convexities, the aim being to ensure that a concavity is arranged between the contact and the cusp degree. In addition, they were posted in the vertical dimension onto the compensation curves. These modifications afforded the abovementioned possibilities.

The cusp slopes were then ground in protrusion, laterotrusion and mediotrusion tracks with a trajectory of inclination of 40°. All cusp portions disturbing a smooth trajectory were planed. The centric contacts were not interrupted by virtue of their arrangement, which in contrast to DE 297 16 622 U1 ensures the vertical spacing and the central relation of the jaws to one another. To achieve a disclusion increasing uniformly from anterior to posterior, the abrasion inclination angles were shaped decreasing by ca. 5° sequentially from anterior to posterior.

It has been found that teeth manufactured according to this method:
1. function without modification in a very large number of cases (>55%);
2. can be tailored individually by simple, subtractive measures, so that they also function in the majority of all cases (>97%);
3. still satisfy the requirement of vertical support after suitable modification;
4. function in all occlusion concepts;
5. require less modification, in the fully balanced and unilaterally balanced occlusion concept, than teeth in the sense of PCT/EP99/06079;
6. are subject to less wear than teeth which centrically are supported not horizontally and vertically, but instead on slanting planes.

The inclination of the abrasion surfaces on the mediotrusion side is preferably 3 to 7 degrees, and in particular 5 degrees, less than on the laterotrusion side.

The inclination of the abrasion surfaces of adjacent teeth can decrease sequentially from anterior to posterior, in particular by in each case 3 to 7 degrees, and preferably by 5 degrees.

Preferred values for the inclination of the abrasion surface for premolar 4 on the mediotrusion side have been found to be between 35 and 42 degrees, in particular 40 degrees. On the laterotrusion side, the preferred angle is 40 to 47 degrees, preferably 45 degrees. The further teeth possibly included in the set of teeth then follow the above scheme in terms of the inclination of their abrasion surfaces.

A set of teeth according to the invention can consist of molars or molars 4, 5, 6 and 7, the inclination of the abrasion surfaces responding to the following scheme:

| | Cusp inclination on the | |
|---|---|---|
| Tooth | mediotrusion side | laterotrusion side |
| 4 | 35°-42°, in particular 40° | 40°-47°, in particular 45° |
| 5 | 30°-37°, in particular 35° | 35°-42°, in particular 40° |
| 6 | 25°-32°, in particular 30° | 30°-37°, in particular 35° |
| 7 | 20°-27°, in particular 25° | 25°-32°, in particular 30° |

BRIEF DESCRIPTION OF THE DRAWINGS

The invention is explained in more detail below with reference to the attached drawings, in which.

DETAILED DESCRIPTION OF THE INVENTION

Figure 1:
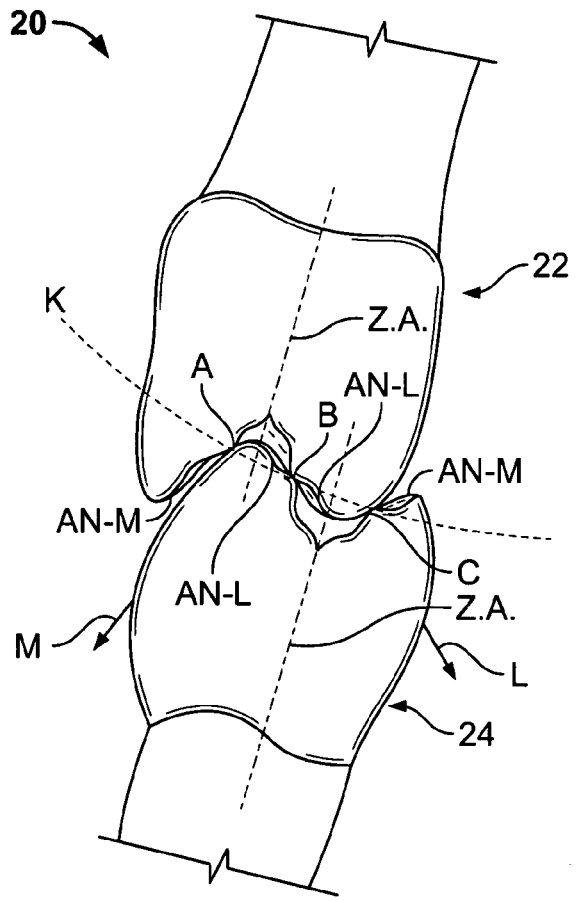
FIG. 1 shows an antagonist pair of premolars 4 in cross section.

A set of teeth 20 consisting of the premolars 4 of the upper jaw and lower jaw 22 and 24, respectively, is shown in FIG. 1, where K designates the transverse compensation curve, Z.A. designates the tooth axis, the arrow M indicates the mediotrusion movement, and the arrow L indicates the laterotrusion movement.

Each tooth has, in the fossa of its respective antagonist, at least three contact points on which its stamp cusps come to rest in the position of intercuspation. The contact points come to rest on spherical sectors and are disposed on the compensation curves defined by the movement of the jaw condyles and are designated by A, B and C. The inclination of the abrasion surfaces is 45° on the laterotrusion side (AN-L) and 40° on the mediotrusion side (AN-M).

Figure 2:
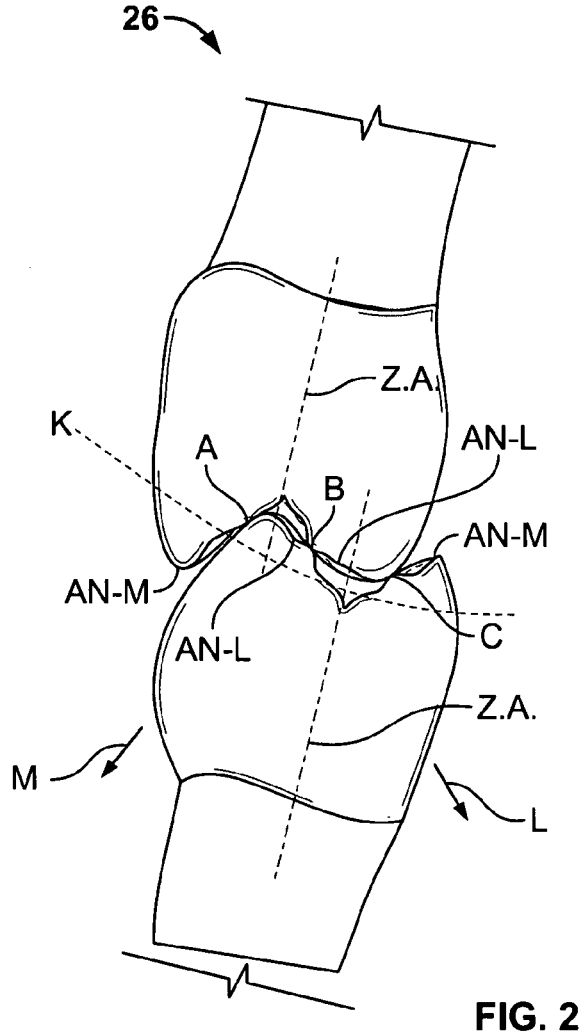
FIG. 2 shows an antagonist pair of premolars 5 in cross section.
Figure 3:
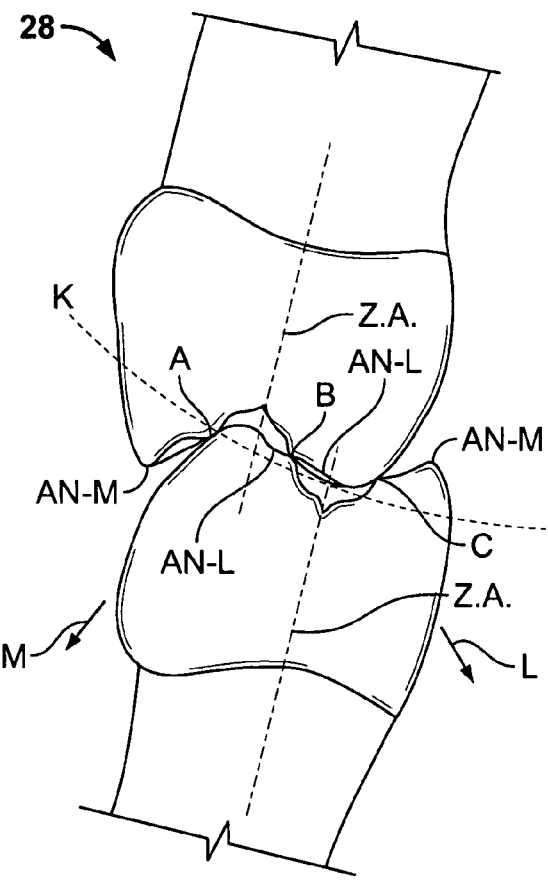
FIG. 3 shows an antagonist pair of molars 6 in cross section.
Figure 4:
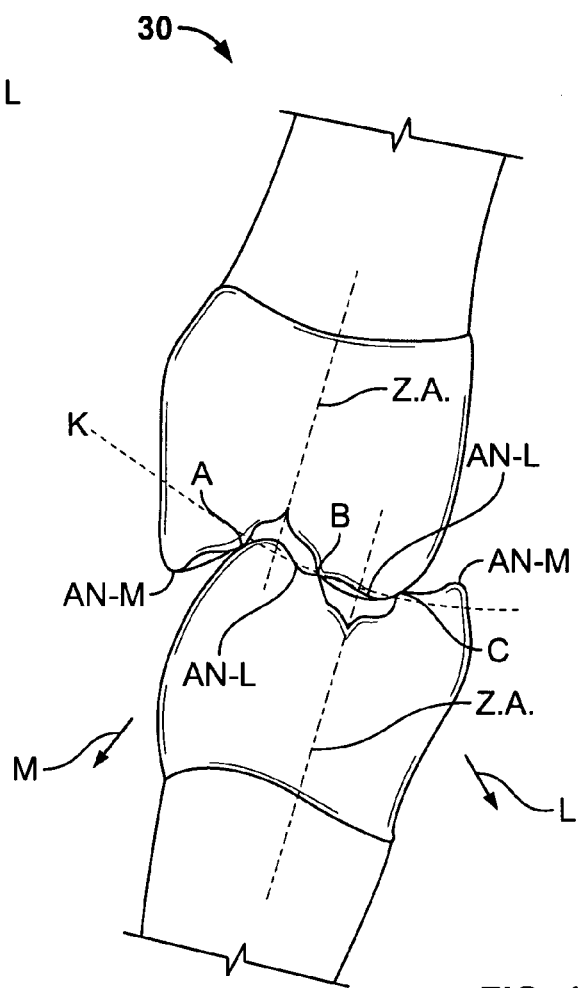
FIG. 4 shows an antagonist pair of molars 7 in cross section.

FIG. 2 shows the antagonist pair 26 adjacent to the antagonist pair from FIG. 1, namely the premolars 5. The inclination of the abrasion surfaces of this pair of teeth, lying posterior to the premolars 4, decreases by a sequence of 5°. (The same applies to the molars 6 and 7, referenced as 28 and 30, respectively—see FIGS. 3 and 4). The inclination of the abrasion surfaces of the premolars 5 is 40° on the laterotrusion side and 35° on the mediotrusion side. Thus, in contrast to Slavicek, an opening of the angle of the entire cusp slope is not necessary, because the configuration of the abrasion surfaces fulfills the objective described by Slavicek without flatter inclination of the entire cusp slope including the centric contacts.

Figure 5:
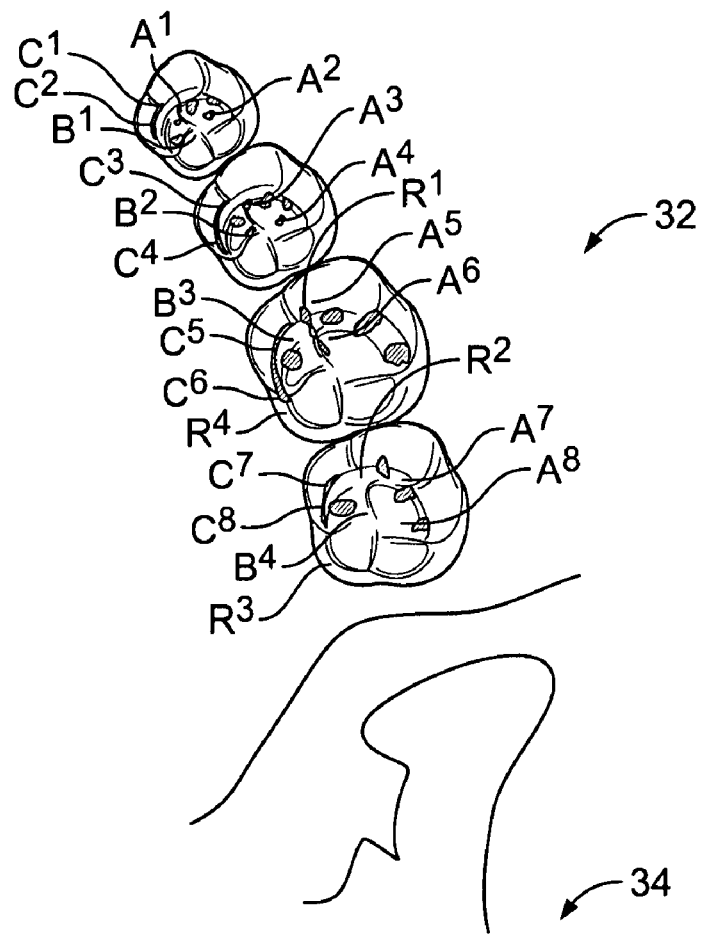
FIG. 5 shows a row of teeth of an upper jaw and a row of teeth of a lower jaw, with the condyle and mandibular fossa.
Figure 5:
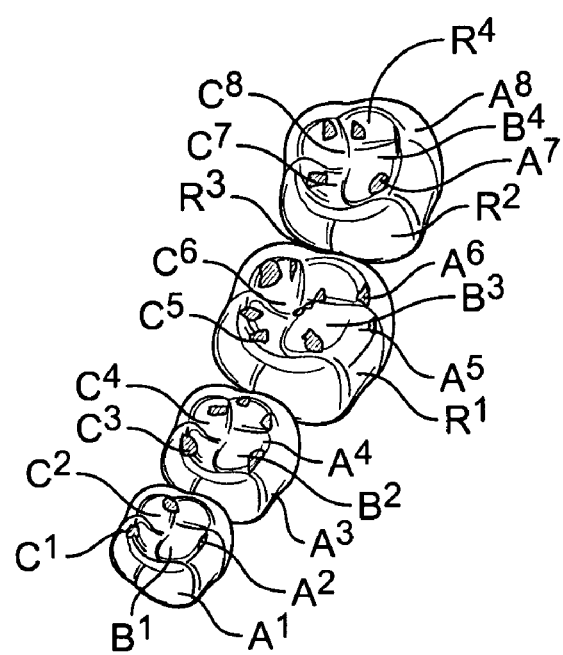

In FIG. 5, showing a row of teeth of the upper and lower jaw 32 and 34, respectively, the centric contacts are designated by $A^1$-$A^8$, $B^1$-$B^4$, $C^1$-$C^8$ and R. The abrasion surfaces according to an embodiment of the invention are shown shaded. By virtue of the concavities surrounding them, the centric contacts remain free-standing.

Figure 6:
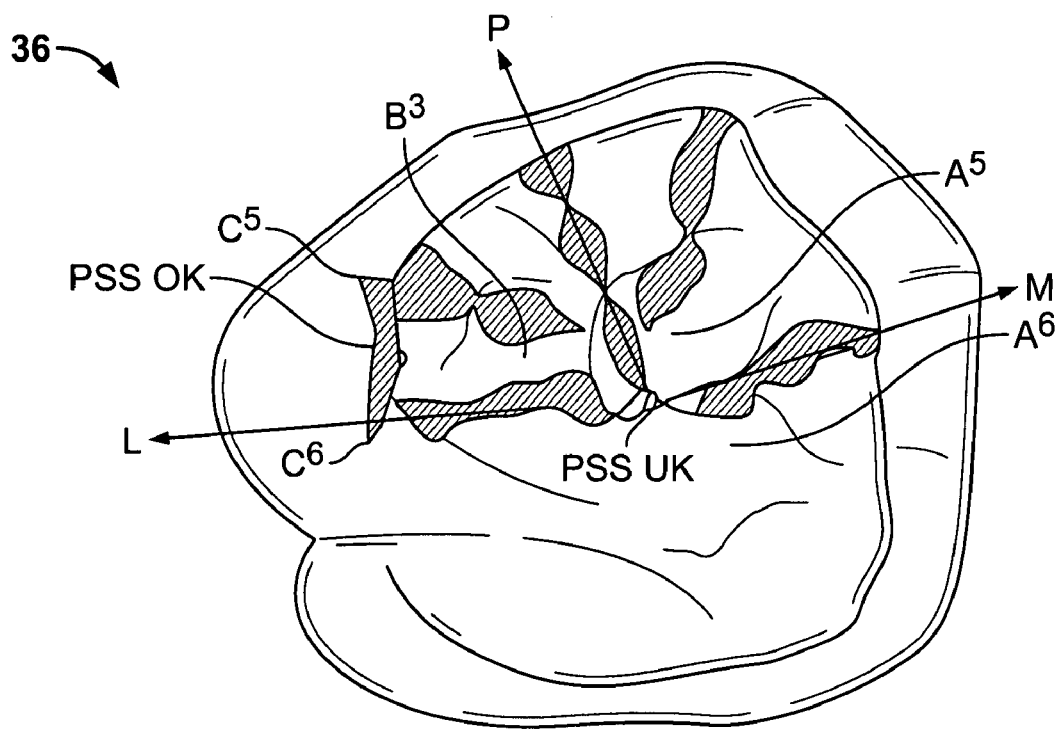
FIG. 6 shows an enlarged detail from FIG. 5.
Figure 6:
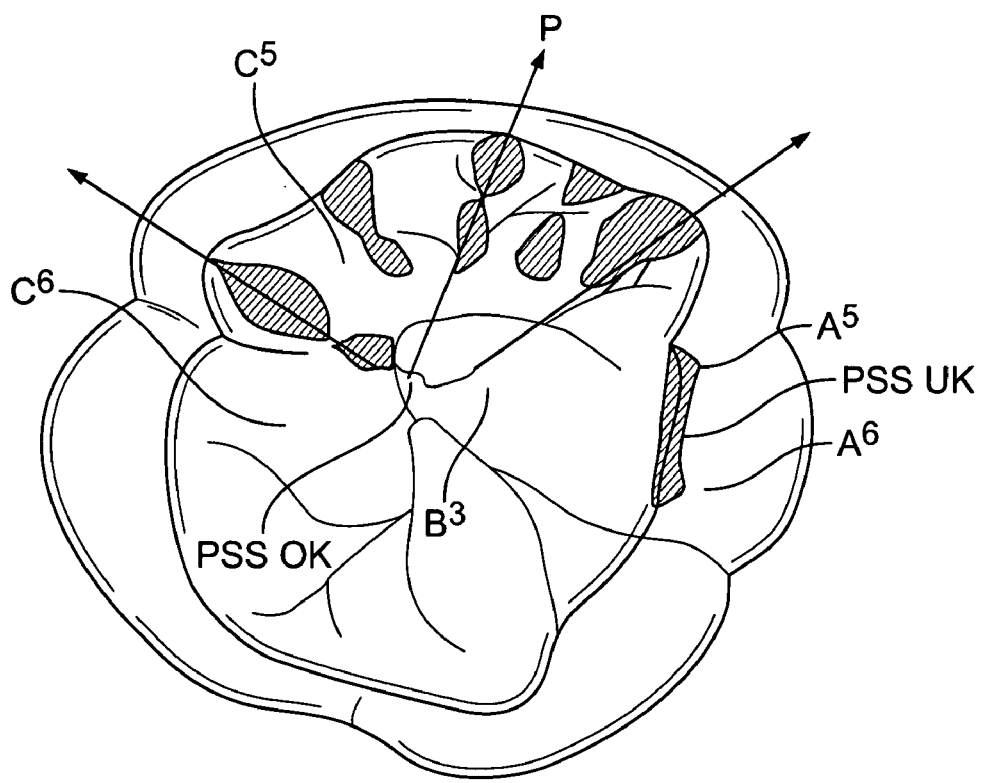

FIG. 6 shows teeth 36 (as enlarged details from FIG. 5) an example of which abrasions are disposed according to an embodiment of the invention on a stamp cusp and an antagonistic fossa in the functional movements. P designates the protrusion movement, M the mediotrusion movement, and L the laterotrusion movement in the arrow direction. PSS OK designates the position of the cusp tip of the upper stamp cusp, and PSS UK designates that of the lower stamp cusp. In this context it should be noted that the details in the figures are not shown true to scale, and the size and angle data cannot be taken from the figures. They have been shown mainly for their illustrative character.

The invention claimed is:

1. A set of pre-manufactured teeth, comprising at least one of a first molar and a premolar selected from a plurality of molars or premolars provided for one jaw, and at least one of a second premolar and a molar selected from a plurality of antagonists provided for the other jaw, wherein at least three centric contact points being provided in each of a fossa of a premolar or a molar, a stamp cusp of the antagonist coming to rest on the contact points in the position of intercuspation, and the contact points being disposed on a compensation curve defined by the movement of the jaw condyles, such that the centric contact points each lie on a spherical sector, and abrasions are disposed in at least one movement track without breaking up at least one of a plurality of punctiform contacts.

2. The set of teeth as claimed in claim 1, wherein an inclination of the abrasion surfaces on the mediotrusion side is between about 3 to about 7 degrees, less than on the laterotrusion side.

3. The set of teeth as claimed in claim 2, wherein the inclination of the abrasion surfaces of adjacent teeth decreases sequentially from anterior to posterior.

4. The set of teeth as claimed in claim 3, wherein the sequential decrease is between about 3 to about 7 degrees.

5. The set of teeth as claimed in claim 1, wherein an inclination of the abrasion surface of a molar 7 on the mediotrusion side is between about 20 and about 27 degrees.

6. The set of teeth as claimed in claim 1, wherein the inclination of the abrasion surface of a molar 7 on the laterotrusion side is between about 25 to about 32 degrees.

7. The set of teeth as claimed in claim 1 further comprising one or more premolars or molars 4, 5, 6 arid 7, wherein the inclination of the abrasion surfaces is provided as follows:

| Tooth | Inlination of abrasion surfaces on the | |
|---|---|---|
| | mediotrusion side | laterotrusion side |
| 4 | 40° | 45° |
| 5 | 35° | 40° |
| 6 | 30° | 35° |
| 7 | 25° | 30°. |

8. The set of teeth as claimed in claim 1, wherein the abrasions are disposed in the movement tracks of latero-protrusion, immediate side shift and retrusive surtrusion.

9. The set of teeth as claimed in claim 1, wherein the abrasions are configured to provide sliding movement without losing central relationship in both a vertical direction and a horizontal direction.

10. The set of teeth as claimed in claim 1, wherein the abrasions are arranged without breaking up at least two of the punctiform contacts.

11. The set of teeth as claimed in claim 1, wherein the abrasions are arranged without breaking up at least three of the punctiform contacts.

12. The set of teeth as claimed in claim 1, wherein cusp slopes are configured having a trajectory of about forty degrees.

13. The set of teeth as claimed in claim 1, wherein the inclination of the abrasion surfaces of adjacent teeth decreases about five degrees sequentially from anterior to posterior.

* * * * *